US007674920B2

(12) United States Patent
Bernabe et al.

(10) Patent No.: US 7,674,920 B2
(45) Date of Patent: Mar. 9, 2010

(54) METHODS FOR PREPARING OXYDIPHTHALIC ANHYDRIDES, OXYDIPHTHALIC ANHYDRIDES PREPARED THEREBY, AND POLYETHERIMIDES DERIVED THEREFROM

(75) Inventors: Beatriz Penalver Bernabe, Chicago, IL (US); Lioba Maria Kloppenburg, Mount Vernon, IN (US); Matt Kuhlman, Evansville, IN (US); Roy Ray Odle, Mount Vernon, IN (US); Eric Pressman, Greenbush, NY (US); Narayan Ramesh, Evansville, IN (US); Harpreet Singh, Evansville, IN (US)

(73) Assignee: Sabic Innovative Plastics IP B.V. (NL)

( * ) Notice: Subject to any disclaimer, the term of this patent is extended or adjusted under 35 U.S.C. 154(b) by 0 days.

(21) Appl. No.: 12/058,331

(22) Filed: Mar. 28, 2008

(65) Prior Publication Data

US 2009/0247725 A1 Oct. 1, 2009

(51) Int. Cl.
*C07D 307/89* (2006.01)
(52) U.S. Cl. .................................... 549/241
(58) Field of Classification Search .............. 549/241
See application file for complete search history.

(56) References Cited

U.S. PATENT DOCUMENTS

| 4,757,149 | A | | 7/1988 | Maresca |
|---|---|---|---|---|
| 4,780,544 | A | | 10/1988 | Berdahl |
| 4,808,731 | A | | 2/1989 | Berdahl et al. |
| 4,870,194 | A | * | 9/1989 | Molinaro et al. ............ 549/241 |
| 4,874,835 | A | | 10/1989 | Berdahl |
| 4,933,469 | A | | 6/1990 | Berdahl et al. |
| 5,021,168 | A | | 6/1991 | Molinaro et al. |
| 6,028,203 | A | | 2/2000 | Brunelle et al. |
| 6,204,394 | B1 | | 3/2001 | Sakata et al. |
| 6,657,067 | B2 | * | 12/2003 | Colborn et al. ............ 548/476 |
| 6,706,897 | B1 | | 3/2004 | Brunelle et al. |
| 6,727,370 | B1 | * | 4/2004 | Brunelle et al. ............ 549/241 |
| 2006/0135791 | A1 | | 6/2006 | Pressman et al. |
| 2006/0293528 | A1 | | 12/2006 | Stella et al. |
| 2007/0073035 | A1 | | 3/2007 | Stella et al. |
| 2007/0073063 | A1 | | 3/2007 | Stella et al. |
| 2007/0073066 | A1 | | 3/2007 | Stella et al. |
| 2007/0117990 | A1 | | 5/2007 | Pressman et al. |

FOREIGN PATENT DOCUMENTS

| CN | 1324794 | | 12/2001 |
|---|---|---|---|
| CN | 1370775 | | 9/2002 |
| CN | 1706846 | | 12/2005 |
| CN | 1827611 | | 9/2006 |
| EP | 1674443 | A1 | 6/2006 |
| JP | 11158168 | | 6/1999 |
| JP | 2005145838 | | 6/2005 |
| JP | 2005350434 | | 12/2005 |
| JP | 2006188502 | | 7/2006 |
| JP | 2006213646 | | 8/2006 |
| WO | WO9827047 | A1 | 6/1998 |
| WO | 2008063206 | A1 | 5/2008 |

OTHER PUBLICATIONS

Wu et al., "Synthesis technology of tetracarboxylic dianhydride monomers for polyimide," (Abstract) Journal Huaxue Yu Nianhe (2002, (4), 173-175, School of Chemistry and Chemical Engineering, Heilongjiang University, Harbin, 150080, Peop. Rep. China.
European Patent Office, PCT International Search Report, International Application No. PCT/US2008/058685, Date of Mailing: Feb. 3, 2009.
European Patent Office, PCT Written Opinion of the ISA, International Application No. PCT/US2008/058685, Date of Mailing: Feb. 3, 2009.

\* cited by examiner

*Primary Examiner*—Bernard Dentz
(74) *Attorney, Agent, or Firm*—Cantor Colburn LLP

(57) ABSTRACT

A method for preparing an oxydiphthalic anhydride comprises contacting, under reactive and substantially anhydrous conditions in a reactor, at least one halophthalic anhydride containing more than 250 ppm chlorophthalide impurity with a carbonate of the formula $M_2CO_3$, wherein M is an alkali metal, in the presence of a catalytic proportion of at least one phase transfer catalyst selected from the group consisting of hexaalkylguanidinium halides and alpha,omega-bis(pentaalkylguanidinium)alkane salts, phosphonium salts, phosphazenium salts, pyridinium salts, phosphazenium salts, ammonium salts, and combinations thereof. The phase transfer catalyst is present in a sufficient amount to prepare the oxydiphthalic anhydride when the chlorophthalide is present in an amount that is more than 250 ppm, and the oxydiphthalic anhydride is produced in a yield, based on the carbonate, of at least 70%.

48 Claims, No Drawings

METHODS FOR PREPARING OXYDIPHTHALIC ANHYDRIDES, OXYDIPHTHALIC ANHYDRIDES PREPARED THEREBY, AND POLYETHERIMIDES DERIVED THEREFROM

BACKGROUND OF THE INVENTION

This invention relates to methods of preparing oxydiphthalic anhydrides, the oxydiphthalic anhydrides prepared thereby, and polyetherimides derived therefrom.

Oxydiphthalic anhydrides, such as 4,4'-oxydiphthalic anhydride, are important monomers for the preparation of polyetherimides having exceptionally high temperature performance and excellent solvent resistance. These properties are useful in high performance plastics applications such as advanced composites and electronic circuit materials.

The preparation of oxydiphthalic anhydrides typically proceeds by the reaction of halophthalic anhydrides with potassium carbonate. Reaction conditions include neat and solvent reactions and the presence of various catalysts. Conventionally, the catalyst is added to the mixture of the halophthalic anhydride and potassium carbonate. Reaction yields vary considerably with impurities in the halophthalic anhydride, for example 4 or 5 or 6 or 7-chlorophthalide (herein referred to simply as chlorophthalide), which can be present in amounts greater than 250 ppm.

It is of interest, therefore, to provide a method for oxydiphthalic anhydride preparation that affords high yields and a minimum of by-products even in the presence of impurities, and provide other improvements to the process, which are consistently and reproducibly applicable.

BRIEF SUMMARY OF THE INVENTION

The disclosed method enables the preparation of oxydiphthalic anhydrides when chlorophthalide (an impurity) is present in the reaction mixture in quantities greater than 250 ppm based on the halophthalic anhydride present in the mixture. Said preparation consistently affords high yields of the desired product and is highly reproducible.

In one embodiment, a method for preparing an oxydiphthalic anhydride comprises contacting, under reactive and substantially anhydrous conditions in a reactor, at least one halophthalic anhydride containing more than 250 ppm chlorophthalide impurity with a carbonate of the formula $M_2CO_3$, wherein M is an alkali metal, in the presence of a catalytic proportion of at least one phase transfer catalyst selected from the group consisting of hexaalkylguanidinium halides and alpha,omega-bis(pentaalkylguanidinium)alkane salts, phosphonium salts, pyridinium salts, phosphazenium salts, ammonium salts, and combinations thereof. The phase transfer catalyst is present in a sufficient amount to prepare the oxydiphthalic anhydride when the chlorophthalide is present in an amount that is more than 250 ppm, and the oxydiphthalic anhydride is produced in a yield, based on carbonate, of at least 70%. The yield, based on carbonate, can also be referred to as the "absolute yield."

In one embodiment, a method for preparing 4,4'-oxydiphthalic anhydride comprises contacting, in a solvent with boiling point greater than about 150° C. under substantially anhydrous conditions in a reactor and at a temperature in the range of about 120° C. to 250° C., 4-chlorophthalic anhydride containing greater than 1000 ppm chlorophthalide impurity with potassium carbonate in the presence of a catalytic proportion of hexaethylguanidinium chloride. The molar ratio of 4-chlorophthalic anhydride to potassium carbonate is in the range of 1.9 to 4 and the proportion of hexaethylguanidinium chloride is in the range of greater than or equal to 2 mol %, and further defined by the formula below based on 4-chlorophthalic anhydride. The chlorophthalic anhydride is present in an amount of x moles, the chlorophthalide is present in an amount z>1000 ppm relative to the chlorophthalic anhydride, and the hexaethylguanidinium chloride is present in a molar percentage amount, Phase Transfer Catalyst mol %, based on the 4-chlorophthalic anhydride, according to the following formula:

$$\text{Phase Transfer Catalyst mol \%} = 100Y(0.02x + (2E-6)z \times K);$$

wherein Y is a number $>=1$, and

K=(MW of 4-chlorophthalic anhydride)/(MW of the chlorophthalide)

The carbonate is present in an amount of about 40 mol % to about 60 mol % relative to 4-chlorophthalic anhydride, and the hexaethylguanidinium chloride is present in a sufficient amount to prepare the 4,4'-oxydiphthalic anhydride when the chlorophthalide is present in an amount that is more than 1000 ppm. The 4,4'-oxydiphthalic anhydride is formed in a yield, based on the potassium carbonate, of greater than 70%.

In one embodiment, a method for preparing an oxydiphthalic anhydride comprises forming a mixture comprising at least one halophthalic anhydride containing greater than 250 ppm chlorophthalide impurity and a catalytic proportion of at least one phase transfer catalyst selected from the group consisting of hexaalkylguanidinium halides and alpha,omega-bis(pentaalkylguanidinium)alkane salts, phosphonium salts, pyridinium salts, phosphazenium salts, ammonium salts, and combinations thereof, and incrementally adding to the mixture, dry powder, or slurry under reactive and substantially anhydrous conditions in a reactor, a carbonate of the formula $M_2CO_3$, wherein M is an alkali metal. The phase transfer catalyst is present in a sufficient amount to prepare the oxydiphthalic anhydride when the chlorophthalide is present in an amount that is more than 250 ppm, and the oxydiphthalic anhydride is formed in a yield greater than 70%, based on the carbonate.

In one embodiment, a method for preparing 4,4'-oxydiphthalic anhydride which comprises forming, in a solvent with boiling point greater than about 150° C., a mixture of 4-chlorophthalic anhydride containing greater than 250 ppm chlorophthalide impurity and a catalytic proportion of hexaethylguanidinium chloride, wherein the proportion of hexaethylguanidinium chloride is in the range of 2 to 10 mole percent based on 4-chlorophthalic anhydride; and incrementally adding, under substantially anhydrous conditions in a reactor and at a temperature in the range of about 120° C. to 250° C., potassium carbonate, wherein the proportion of potassium carbonate is in the range of 48 mol % to 52 mol % based on 4-chlorophthalic anhydride, wherein the hexaethylguanidinium chloride is present in a sufficient amount to prepare the 4,4'-oxydiphthalic anhydride when the chlorophthalide is present in an amount that is more than 250 ppm, and the 4,4'-oxydiphthalic anhydride is formed in a yield greater than 75%, based on the potassium carbonate.

In another embodiment is disclosed an oxydiphthalic anhydride prepared by the method described herein.

In another embodiment is disclosed a polyetherimide derived from an oxydiphthalic anhydride prepared by the method described herein.

DETAILED DESCRIPTION OF THE INVENTION

The invention is based on the unexpected discovery that it is now possible to practice a method for preparing an oxydiphthalic anhydride at high yields under conditions that would ordinarily be considered unsuitable, e.g. a high level of impurities in the starting materials, by the use of additional catalysts. It is surprising that the additional use of catalyst would increase the yields, because ordinarily, the additional use of catalyst increases only the rate of the reaction. The invention is also based on the discovery that staged (slow) addition of carbonates, as compared to a unstaged batch (direct/fast) addition of carbonate, under conditions containing impurities, have an unexpected beneficial effect on the yield.

A method for preparing an oxydiphthalic anhydride comprises contacting, under reactive and substantially anhydrous conditions in a reactor, at least one halophthalic anhydride containing more than 250 ppm chlorophthalide impurity, based on the halophthalic anhydride, with a carbonate of the formula $M_2CO_3$, M being an alkali metal, in the presence of a catalytic proportion of at least one phase transfer catalyst selected from the group consisting of hexaalkylguanidinium halides and alpha,omega-bis(pentaalkylguanidinium)alkane salts, phosphonium salts, pyridinium salts, phosphazenium salts, ammonium salts, and combinations thereof. The phase transfer catalyst is present in a sufficient amount to prepare the oxydiphthalic anhydride when the chlorophthalide is present in an amount more than 250 ppm, even more particularly more than 1000 ppm, and most particularly more than 5000 ppm. The oxydiphthalic anhydride is produced in a yield, based on the carbonate, of at least 70%.

In one embodiment, the halophthalic anhydride is present in an amount of x moles, the chlorophthalide is present in an amount z>1000 ppm relative to the halophthalic anhydride, and the phase transfer catalyst is present in a molar percentage (mol %, mole %) amount, Phase Transfer Catalyst mol %, based on the halophthalic anhydride, according to the following formula:

Phase Transfer Catalyst mol %=$100Y(0.02x+(2E-6)z \times K)$;

wherein Y is a number >=1, and

K=(MW of halophthalic anhydride)/(MW of the chlorophthalide)

In the above formula, MW refers to molecular weight, $2E-6$ equals the factor $2 \times 10^{-6}$, Y is a number greater than or equal (>=) to 1, not necessarily an integer. It is understood that adjacent factors are multiplied together. Y ranges from 1 to 20, more particularly 1 to 5, and most particularly 1 to 1.1.

Chlorophthalide is a mixture of impurities formed in the preparation of chlorophthalic anhydrides by oxidation of chloroxylenes, and can comprise up to four isomers represented by the general structure (I):

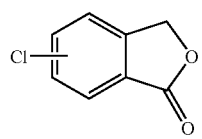

(I)

Herein, the mixture is referred to simply as chlorophthalide.

The oxydiphthalic anhydrides that may be prepared by the disclosed method include 4,4'-oxydiphthalic (hereinafter sometimes designated "4-ODPA"), 3,3'-oxydiphthalic and 3,4'-oxydiphthalic anhydrides. The organic reagents from which the oxydiphthalic anhydrides are derived are, respectively, 4-halophthalic, 3-halophthalic and a mixture of 3- and 4-halophthalic anhydrides. 4-ODPA, is also referred to simply as ODPA, and frequent reference to it will be made hereinafter. It should be understood, however, that one of the other isomers may be substituted for 4-ODPA where appropriate. The halophthalic anhydride can therefore be 3-chlorophthalic anhydride, 4-chlorophthalic anhydride or a mixture thereof. Most particularly, the halophthalic anhydride is 4-chlorophthalic anhydride.

Any halogen may be present in the halophthalic anhydride. Most often the fluoro-, chloro-, or bromophthalic anhydride is employed, with the 4-chlorophthalic anhydride (4-ClPA) being preferred by reason of its relatively low cost and particular suitability.

The reaction producing 4-ODPA is effected through the use of at least one carbonate of the formula $M_2CO_3$, in which M is an alkali metal such as sodium, potassium, rubidium or cesium. Mixtures of such carbonates may be employed. For optimum product yield, it is preferred to employ carbonates of alkali metals having an atomic number of at least about 19. In one embodiment, M is potassium (K). The carbonate is present in an amount of about 40 to about 60 mol % relative to the halophthalic anhydride.

The carbonate can have the form of a powder, granule, flake, or other solid form. As such, in one embodiment can be selected from the group consisting of powdered carbonates, granular carbonates, flaked carbonates, and combinations thereof. In one embodiment, the carbonate is in the form of a powder ranging in size from 0.1 micrometers to 500 micrometers. Particle size of the carbonate can have an effect on product yield. Thus, powdered potassium carbonate has been shown to produce a higher yield of oxydiphthalic anhydride than granular potassium carbonate in the same time period. By reason of the deleterious effect of water on the reaction, it is important when powdered potassium carbonate is used that it first be thoroughly dehydrated. In one embodiment, the carbonate is present in an amount of about 45 to about 53 mol % relative to halophthalic anhydride. In one embodiment, the carbonate is present in an amount of about 50 to about 53 mol % relative to halophthalic anhydride.

Contact between the halophthalic anhydride and the carbonate is under reactive conditions, generally including temperatures in the range of about 120° C. to 250° C. and preferably about 170° C. to 250° C., at atmospheric pressure and a molar ratio of halophthalic anhydride to carbonate in the range of 1.9 to 4.0:1, more particularly 2.0 to 2.4:1. In the preferred range of 2.0 to 2.4:1, the desired product is obtained in high yield.

In one embodiment the carbonate is added to a mixture of the halophthalic anhydride and the phase transfer catalyst at a reaction temperature. In another embodiment the catalyst is added to a mixture of the halophthalic anhydride and the carbonate at a reaction temperature. As shown herein, higher yields are favored by addition of the carbonate to a mixture of halophthalic anhydride and phase transfer catalyst.

The reaction may be performed in the absence or in the presence of at least one solvent. In various embodiments it is preferred that the reaction be conducted in a solvent. While dipolar aprotic solvents may be used, their use is generally not advisable since they can promote side reactions and the formation of colored by-products. In various embodiments suitable solvents have a boiling point above about 120° C., preferably above about 150° C. and more preferably above about 180° C. Exemplary solvents of this type include, but are not limited to, ortho-dichlorobenzene (o-dichlorobenzene, oDCB), para-dichlorobenzene, sulfolane, dimethylacetamide, dichlorotoluene, 2,4-dichlorotoluene, 1,2,4-dichlorobenzene, diphenyl sulfone, phenetole, anisole and veratrole, n-methylpyrrolidine and mixtures thereof. It is more preferred that chlorinated aromatic liquids be employed as solvents, examples of which include, but are not limited to, ortho-dichlorobenzene, 2,4-dichlorotoluene and 1,2,4-trichlorobenzene. 2,4-Dichlorotoluene is often favored because its use minimizes reaction time and product decomposition. Most particularly, the solvent is o-dichlorobenzene, which allows the proportion of phase transfer catalyst to be increased and/or the reaction to be run at super-atmospheric pressure to permit higher temperatures and higher reaction rates.

The reaction mixture should be substantially anhydrous, the term "substantially anhydrous" denoting a total water content of less than about 50, preferably less than about 20 and most preferably less than about 10 ppm by weight. Any water present above this amount can inhibit the reaction, irrespective of its source. Traces of water may be present in either of the reagents (halophthalic anhydride or $M_2CO_3$) or the catalyst. Water should be carefully removed by drying before beginning the reaction. Further, the reagents and/or catalysts can each be dried individually before being combined. Drying can be achieved by methods known in the art. Liquid reagents and solvents can be dried by distillation and/or by contact with molecular sieves, and solid materials such as the carbonate and bicarbonate by heating in an oven, most often under vacuum. More particularly, drying of o-dichlorobenzene (oDCB) is accomplished by distillation of the water/oDCB azeotrope.

In one embodiment the phase transfer catalyst is selected from the group consisting of hexaethylguanidinium chloride, hexaethylguanidinium bromide, hexa-n-butylguanidinium bromide, 1,6-bis(N,N',N',N'',N''-penta-n-butylguanidinium) hexane dibromides, 1,6-bis(N-n-butyl-N',N',N'',N''-tetraethylguanidinium)hexane dibromides, and mixtures thereof. Such phase transfer catalysts are known in the art; reference is made, for example, to U.S. Pat. No. 5,229,482. Hexaalkylguanidinium halides are generally preferred, with hexaethylguanidinium halides being more preferred and hexaethylguanidinium chloride most preferred. In another embodiment, the phase transfer catalyst is tetraphenylphosphonium bromide. It has been found that when a guanidinium salt is employed as a catalyst, the reaction is faster than when a phosphonium salt is employed, yielding an equivalent yield in a substantially shorter time.

The proportion of guanidinium salt employed is usually in the range of about 0.2 to 10.0, preferably about 1 to 3, mole percent based on halophthalic anhydride. For optimum yield with minimum product decomposition over time, the most preferred proportion is in the range of about 2 to 2.5 mole percent when the chlorophthalide level is less than 1000 ppm. When the chlorophthalide level is greater than or equal to 1000 ppm, catalyst level is defined by the equation in paragraph 7. The phase transfer catalyst can also be added to the reactor as a solid or as an aqueous solution that is subsequently dried. The aqueous solution can be dried by any suitable way. In one embodiment, the aqueous solution is dried by contacting the aqueous solution with a solvent. e.g., ortho-dichlorobenzene, toluene, and then heating the resulting solution under conditions sufficient to remove the water.

In another aspect, higher yields of ODPA are obtained by pre-treating the reactor. In one embodiment, the reactor is pre-treated by the sequential steps of (i) adding a caustic solution; (ii) adding water to form an aqueous mixture; and (iii) removing the aqueous mixture; wherein the sequential steps (i) to (iii) are performed one or more times until the aqueous mixture has a pH of less than or equal to 7, and the phase transfer catalyst is added in an aqueous solution after the pre-treatment. In one embodiment, the sequential steps (i) to (iii) are performed 1 to 5 times. In one embodiment the sequential steps (i) to (iii) are performed 1 to 2 times. The caustic solution can comprise any alkali metal hydroxide, in particular an aqueous solution of sodium hydroxide, wherein the sodium hydroxide is present in an amount ranging from 1 to 20 weight percent (wt %).

The oxydiphthalic anhydride can be prepared in batch mode on a scale exceeding 2 kilograms (kg) per batch. Alternatively, when operating in a continuous mode, the oxydiphthalic anhydride can be prepared on a scale exceeding 2 kilograms (kg) per hour In one embodiment the oxydiphthalic anhydride is prepared on a scale greater than 100 kg per batch (in batch mode or per hour in continuous mode), more particularly 2721 kg (3 tons), even more particularly 4536 kg (5 tons), even more particularly 9072 kg (10 tons), even more particularly 13608 kg (15 tons), and most particularly 18144 kg (20 tons). The yield of oxydiphthalic anhydride is greater than 70%, more particularly greater than 80%, and even more particularly greater than 85%, and even more particularly greater than 90%, based on the carbonate. As such, the yield of oxydiphthalic anhydride can range from more than 70% to 90%, or more than 90%, based on the carbonate. In one embodiment, the yield of oxydiphthalic anhydride can range from more than 70% to 99.99%, based on the carbonate.

When the reaction between halophthalic anhydride and carbonate is complete, the product may be isolated by conventional techniques. It is often convenient to merely cool the solution in solvent after filtration while hot, whereupon the desired oxydiphthalic anhydride precipitates and may be removed by filtration.

In a more specific embodiment, a method of preparing 4,4'-oxydiphthalic anhydride comprises contacting, in a solvent with a boiling point greater than about 150° C. under substantially anhydrous conditions in a reactor and at a temperature in the range of about 120° C. to 250° C., 4-chlorophthalic anhydride containing greater than 1000 ppm chlorophthalide impurity (z in the formula below >1000 ppm) with potassium carbonate in the presence of a catalytic proportion of hexaethylguanidinium chloride, the molar ratio of 4-chlorophthalic anhydride to potassium carbonate being in the range of 1.9 to 4, and the proportion of hexaethylguanidinium chloride being in the range greater than or equal to 2 mol % and further determined by the formula below based on 4-chlorophthalic anhydride. The 4-chlorophthalic anhydride is present in an amount of x moles, the chlorophthalide is present in an amount "z" greater than (>) 1000 ppm relative to the 4-chlorophthalic anhydride, and the hexaethylguanidinium chloride is present in a molar percentage amount, Phase Transfer Catalyst mol %, based on the 4-chlorophthalic anhydride, according to the following formula:

Phase Transfer Catalyst mol %=100$Y$(0.02$x$+(2$E$–6)$z$×$K$);

wherein $Y$ is a number >=1, and
$K$=(MW of 4-chlorophthalic anhydride)/(MW of the chlorophthalide).

The carbonate is present in an amount of about 40 mol % to about 60 mol % relative to 4-chlorophthalic anhydride. The hexaethylguanidinium chloride is present in a sufficient amount to prepare the 4,4'-oxydiphthalic anhydride when the chlorophthalide is present in an amount z more than 1000 ppm, and the 4,4'-oxydiphthalic anhydride is formed in a yield, based on the potassium carbonate, of greater than 70%. Y ranges from 1 to 20, more particularly 1 to 5, and most particularly 1 to 1.1. In one embodiment, the potassium carbonate is added as a powder to a mixture of 4,4'-oxydiphthalic anhydride and hexaethylguanidinium chloride. In one embodiment, the solvent is ortho-dichlorobenzene, 2,4-dichlorotoluene or 1,2,4-trichlorobenzene. The molar ratio of 4-chlorophthalic anhydride to potassium carbonate more particularly ranges from 2 to 2.2, and even more particularly from 2 to 2.1. In one embodiment, the carbonate is present in an amount of about 45 to about 53 mol % relative to 4-chlorophthalic anhydride.

Also disclosed is a staged carbonate method of preparing an oxydiphthalic anhydride wherein the carbonate is incrementally added to the reaction mixture at a reaction temperature. The staged carbonate method comprises forming a mixture comprising at least one halophthalic anhydride containing greater than 250 ppm chlorophthalide impurity and a catalytic proportion of at least one phase transfer catalyst selected from the group consisting of hexaalkylguanidinium halides and alpha,omega-bis(pentaalkylguanidinium) alkane salts, phosphonium salts, pyridinium salts, phosphazenium salts, ammonium salts, and combinations thereof; and incrementally adding to the mixture, dry powder, or slurry under reactive and substantially anhydrous conditions in a reactor, a carbonate of the formula $M_2CO_3$, wherein M is an alkali metal; wherein, the phase transfer catalyst is present in a sufficient amount to prepare the oxydiphthalic anhydride when the chlorophthalide is present in an amount that is more than 250 ppm, and the oxydiphthalic anhydride is formed in a yield greater than 70%, based on the carbonate. In one embodiment of the staged carbonate method, the halophthalic anhydride is present in an amount of x moles, the chlorophthalide is present in an amount z greater than or equal to 1000 ppm relative to the halophthalic anhydride, and the phase transfer catalyst is present in a molar percentage amount, Phase Transfer Catalyst mol %, based on the halophthalic anhydride, according to the following formula:

Phase Transfer Catalyst mol %=$100Y(0.02x+(2E-6)z \times K)$;

wherein Y is a number >=1, and

K=(MW of halophthalic anhydride)/(MW of the chlorophthalide).

Y ranges from 1 to 20, more particularly 1 to 5, and most particularly 1 to 1.1. In another embodiment, x is an number ranging from 10 to 1000, and z ranges from 1000 to 25000 ppm. The number of stages can range from 1 to 20, and more particularly 1 to 15, and even more particularly 1 to 10, and most particularly 1 to 6. In one embodiment the carbonate is added to the mixture in 2 to 6 stages, or continuously over 0.5 hours to 15 hours, at a temperature of 120° C. to 250° C.

The carbonate can be staged during either batch mode or continuous mode preparations of the oxydiphthalic anhydride, and on a scale exceeding 2 kilograms per batch (in batch mode) or per hour in continuous mode, more particularly 100 kilograms per batch or per hour. As previously described, the amount of carbonate ranges from about 40 mol % to about 60 mol % relative to halophthalic anhydride.

Previously described embodiments and limitations pertaining to halophthalic anhydride, alkali metal, solvent, phase transfer catalyst, and yields in the preparation of ODPA also apply to the staged carbonate addition method of preparing ODPA. In one staged carbonate embodiment, the halophthalic anhydride is 3-chlorophthalic anhydride, 4-chlorophthalic anhydride, or a mixture thereof. In one staged carbonate embodiment, the halophthalic anhydride is 4-chlorophthalic anhydride. In one staged carbonate embodiment, M is potassium. In one staged carbonate embodiment, a solvent is also present. In one staged carbonate embodiment, the solvent is at least one member selected from the group consisting of ortho-dichlorobenzene, para-dichlorobenzene, sulfolane, dimethylacetamide, dichlorotoluene, 2,4-dichlorotoluene, 1,2,4-dichlorobenzene, diphenyl sulfone, phenetole, anisole and veratrole, and mixtures thereof. In one staged carbonate embodiment, the solvent is ortho-dichlorobenzene, 2,4-dichlorotoluene, or 1,2,4-trichlorobenzene. In one staged carbonate embodiment, the phase transfer catalyst is selected from the group consisting of hexaethylguanidinium chloride, hexaethylguanidinium bromide, hexa-n-butylguanidinium bromide, 1,6-bis(N,N',N',N'',N'''-penta-n-butylguanidinium) hexane dibromides, 1,6-bis(N-n-butyl-N',N',N'',N'''-tetraethylguanidinium)hexane dibromides, phosphonium salts, pyridinium salts, phosphazenium salts, ammonium salts, and combinations thereof. In one staged carbonate embodiment, the phase transfer catalyst is tetraphenylphosphonium bromide. In one staged carbonate embodiment, the yield is greater than 80%, based on the carbonate. In one staged carbonate embodiment, the yield is greater than 85%, based on the carbonate. In one staged carbonate embodiment, the yield is greater than 90%, based on the carbonate. In one embodiment, the yield ranges from more than 80% to 99.99%

In a more specific embodiment of staging the carbonate, a method for preparing 4,4'-oxydiphthalic anhydride comprises forming, in a solvent with boiling point greater than about 150° C., a mixture of 4-chlorophthalic anhydride containing greater than 250 ppm chlorophthalide impurity and a catalytic proportion of hexaethylguanidinium chloride, wherein the proportion of hexaethylguanidinium chloride is in the range of 2 to 10 mole percent based on 4-chlorophthalic anhydride; and incrementally adding, under substantially anhydrous conditions in a reactor and at a temperature in the range of about 120° C. to 250° C. potassium carbonate, wherein the proportion of potassium carbonate is in the range of 48 mol % to 52 mol % based on 4-chlorophthalic anhydride. The hexaethylguanidinium chloride is present in a sufficient amount to prepare the 4,4'-oxydiphthalic anhydride when the chlorophthalide is present in an amount that is more than 250 ppm, and the 4,4'-oxydiphthalic anhydride is formed in a yield greater than 75%, based on the potassium carbonate. In one embodiment, the 4,4'-oxydiphthalic anhydride is present in an amount of x moles, the chlorophthalide is present in an amount z greater than 1000 ppm, and the hexaethylguanidinium chloride is present in a molar percentage (mol %) amount, Phase Transfer Catalyst mol %, based on the halophthalic anhydride, according to the following formula:

Phase Transfer Catalyst mol %=$100Y(0.02x+(2E-6)z \times K)$;

wherein Y is a number >=1, and

K=(MW of 4-chlorophthalic anhydride)/(MW of the chlorophthalide).

Y ranges from 1 to 20, more particularly 1 to 5, and most particularly 1 to 1.1.

Further disclosed herein is an oxydiphthalic anhydride prepared by the above described methods.

Also disclosed is a polyetherimide derived from an oxydiphthalic anhydride prepared by the disclosed methods.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

All parts and percentages are by weight unless otherwise designated. Chemicals and solvents were reagent grade, and were carefully dried and otherwise used without purification. Solvents were dried over activated 4 A molecular sieves or azeotropically dried before use. Granular or powdered potassium carbonate was dried in a vacuum oven overnight before use. Analysis was performed by using a reverse phase High Pressure Liquid Chromatography (HPLC) calibrated using authentic standards.

EXAMPLES

Examples 1 to 8

Chlorophthalide Impurity Level

The following examples demonstrate the deleterious effect of chlorophthalide impurity on the reaction yield of oxydiphthalic anhydride, obtained from the reaction of 4-chlorophthalic anhydride (4-ClPA), understood to be a mixture of the 3-chloro and 4-chloro isomers, and $K_2CO_3$ in the presence of a phase transfer catalyst, hexaethylguanidinium chloride (HEGCl). Surprisingly, the data further show that for starting material containing an increased level of chlorophthalide impurity, the yield of oxydiphthalic anhydride increases when the level of catalyst is increased.

Reagent grade o-dichlorobenzene (oDCB) was used as received from Fisher Scientific. Material used in the glovebox had been stored over 4 A molecular sieves and checked for water levels of less than 10 ppm via Karl-Fischer (KF) titrations (described below). Two samples of solid 4-chlorophthalic anhydride (4-ClPA) were obtained: One sample contained a low level of chlorophthalide impurity that was less than 250 ppm and a second sample had a chlorophthalide impurity that was more than 250 ppm. 4-ClPA can be obtained from vendors such as Aldrich, Jiangsu Tianyin Chemical Industry Co., Ltd., Dynamic International Enterprises Limited, Harbin Times, Wisechem International Co., Ltd., TCI Europe NV, Infine Chemicals Co., Limited, Shanghai Sunwise Chemical Co., Clariant, Ltd., Connect Marketing GmbH, NSTU Chemicals Hangzhou Co. and AK Scientific, Inc.

An oDCB solution of phase transfer catalyst hexaethylguanidinium chloride (HEGCl) was prepared from a HEGCl-brine mixture which had a composition of about 35% HEGCL in the brine solution. (obtained from Vandermark Corporation) in the pilot facility on a >350 liter. Additional 4 A molecular sieves were added to the solution to ensure low moisture levels of less than 10 ppm, and the material was stored in a glove box. Commercially available $K_2CO_3$, obtained from Armand Corporation (Oxychem), was dried at 220° C. in a Kugelrohr oven overnight and stored in the glove-box. Extra fine particle size was used, identical to material used on a greater than 100 gal (379 liter) scale.

The following methods/techniques were used in Examples 1 to 8.

Karl-Fischer Titrations (KF). A sample of approximately 5 mL of solvent was obtained (from an oDCB distillate) taking care to ensure that the sample was dry. A 1 ml syringe was carefully filled with the solvent and care was taken to avoid the formation of air bubbles. This sample was then injected into the KF titrator. The titration was carried out automatically by the analyzer, and results are recorded in ppm water.

One Pot ODPA reaction using pure 4-ClPA with <250 ppm chlorophthalide):

All glassware was thoroughly dried in an oven at 120° C. prior to use. Flaked 4-ClPA (31.6 g; 0.173 mol, stored in glove box) and 12.0 g $K_2CO_3$ (0.087 mol; Kugelrohr dried; stored in glove box) was weighed out into a 250 ml three-neck round-bottom flask, which was equipped with a Dean-Stark trap with a condenser, a mechanical stirrer, and a nitrogen inlet. o-Dichlorobenzene (109 g) was added, which had been dried over 4 A molecular sieves (<5 ppm of water via KF titration). 4-ClPA completely dissolved in oDCB upon heating. The mixture was heated at reflux (210° C. oil bath temperature) for half an hour under a nitrogen atmosphere and 20 g of oDCB was distilled off. Reaction dryness was determined by sampling the distillate as <10 ppm water via KF. The nitrogen inlet was switched to a septum and nitrogen was allowed through the apparatus via the condenser opening. HEGCl/oDCB solution (6.4 mL, 11.45 wt %, 0.0038 mol) was slowly syringed into the reaction mixture. Vigorous $CO_2$ evolution occurred and the reaction turned yellow in color immediately. An additional 30 g of oDCB was distilled off. The reaction was allowed to stir at 210° C. oil bath temperature for 6 hours. The reaction mixture was sampled periodically and the normalized yield was analyzed using an HPLC method to monitor reaction yield. In addition to oxydiphthalic anhydride (ODPA), oxyphthalic diacid dianhydride (ODDA) and oxydiphthalic tetraacid (ODTA) are also formed. The normalized yield presented in the results is defined as follows: Normalized Yield %=100*2*(moles ODPA formed+moles ODDA formed+moles ODTA formed)/((2*(moles ODPA formed+moles ODDA formed+moles ODTA formed)+moles ClPA remaining+moles OHPA formed), in a sample of the reaction mixture, where "*" means the factors are multiplied. Moles for each component were calculated from the HPLC determined wt % of that component divided by component MW.

One Pot ODPA Reaction Using ClPA (impure 4-ClPA with >250 ppm chlorophthalide):

All glassware was thoroughly dried in an oven at 120° C. prior to use. 4-ClPA in oDCB (147.66 g, 0.173 mol, 21.4% in 4-ClPA, containing 0.254% chlorophthalic acid (ClDA) and 16 g extra oDCB (dried over molecular sieves; <5 ppm of water via KF titration) was weighed into a 250 ml three-neck round-bottom flask, which was equipped with a Dean-Stark trap with a condenser, a mechanical stirrer, and a nitrogen inlet. The mixture was heated at reflux (210° C. oil bath temperature) under nitrogen atmosphere and a total of 35.7 g of oDCB was distilled off when a reaction dryness of <10 ppm water was determined via KF by sampling distillate. The flask was taken into the glove-box and 12.0 g of $K_2CO_3$ (0.087 mol; Kugelrohr dried; stored in glove box) was weighed out and added to the dry 4-ClPA solution. The carbonate was rinsed into the flask with an additional 2 g of oDCB (stored over molecular sieves; <5 ppm of water). The nitrogen inlet was replaced with a septum. Outside the glove-box, the mixture was heated back up to 210° C. oil bath temperature. HEGCl/oDCB solution (6.0 mL, 13.3 wt %, 0.0038 mol of HEGCl), stored over molecular sieves in glove box, was slowly syringed into the reaction mixture. Vigorous carbon dioxide evolution occurred and the reaction turned yellow in color immediately. The septum was replaced quickly with the nitrogen inlet again and an additional 15.3 g of oDCB was distilled of under a nitrogen purge. The reaction was allowed to stir at 210° C. oil bath temperature for 6 hours. The reaction mixture gradually turned dark yellow to greenish-grey. Roughly every 2 hours a 0.1 g sample was taken with a dry glass pipette for HPLC yield analysis. All reactions using oDCB solutions of 4-ClPA containing varying levels of chlorophthalide were performed in this manner. Amounts and yield calculations can be found in Table 1.

Example 1 was performed using flaked 4-ClPA having a chlorophthalide level that was less than 250 ppm. Examples 2-4 were performed using flaked 4-ClPA having a chlorophthalide level that was more than 250 ppm. The actual level of chlorophthalide level used in Examples 2-4 are shown in Table 1.

TABLE 1

Effect of increased level of chlorophthalide on reaction yield at 2.2 mol % catalyst

| EXAMPLE | Chlorophthalide (ppm) Relative to 4-ClPA | Catalyst Level (mol % HEGCl Catalyst based on CIPA) | Normalized Yield (%) | Absolute Yield (based on carbonate)[1] |
|---|---|---|---|---|
| 1 | 250 | 2.2 | 92* | 77-90 |
| 2 | 2443 | 2.2 | 83.5* | 68.5-81.5 |
| 3 | 4096 | 2.2 | 72.5* | 57.5-70.5 |
| 4 | 7072 | 2.2 | 39 | 24-37 |

*Average of 2 or more reactions.
[1]Normalized yield and absolute yield (based on carbonate) are theoretically identical. In practice, there is a discrepancy in the actual normalized yield that is actually reported above and the absolute yield (based on carbonate). The absolute yield in practice, based on carbonate, can be determined by the formula 100 * (moles ODPA formed + moles ODDA formed + moles ODTA formed)/moles of carbonate charged in the reaction mixture. Historically, the absolute yield, based on carbonate, was approximately 2-15% lower than the Normalized Yield.

In Table 1, Normalized Yield %=100*2*(moles ODPA formed+moles ODDA formed+moles ODTA formed)/((2*(moles ODPA formed+moles ODDA formed+moles ODTA formed)+moles ClPA remaining+moles OHPA formed), where "*" means the factors are multiplied. Moles for each component were calculated from the HPLC determined wt % of that component divided by component MW.

Table 1 demonstrates the deleterious effect of chlorophthalide on the yield of oxydiphthalic anhydride at constant catalyst level of 2.2 mol %. In Example 1, the 4-ClPA had the lowest level of chlorophthalide impurity, 250 ppm, and produced the highest yield, 92%. In Examples 2 to 4, using less pure 4-ClPA, the yield gradually drops to a low of 39% at the highest chlorophthalide level, 7072 ppm. All the yields are reported at 4 hours for ease of comparison.

Table 2 demonstrates the loss of yield of oxydiphthalic anhydride caused by the chlorophthalide impurity can be compensated for by the addition of catalyst. The improved yield with higher catalyst level is surprising because typically, the use of additional catalyst would be expected to improve the rate of reaction, not the yield. Previous Examples 1 and 4 are included in Table 2 for ease of comparison. Example 1 shows the base case having the lowest impurity level, 250 ppm, yielding 92% at a catalyst level of 2.2 mol %. Comparing Examples 4 and 8, each having a high chlorophthalide level of 7072 ppm, the yield of ODPA increased from 39% to 78% when the catalyst level was increased from 2.2 mol % to 2.9 mol %, respectively. Examples 6 and 7 having a chlorophthalide impurity level of 3551 ppm, show a similar improvement in yield, from 77% to 91%, when the catalyst level was raised of 2.6 mol % to 3.1 mol %, respectively. All the yields are reported at 4 hours for ease of comparison.

TABLE 2

| EXAMPLE | Chlorophthalide (ppm) | Catalyst Level (mol % Catalyst/ based on CIPA) | Normalized Yield (%) | Yield (Based on carbonate)[1] |
|---|---|---|---|---|
| 1 | 250 | 2.2 | 92 | 77-90 |
| 6 | 3551 | 2.6 | 77 | 62-75 |
| 7 | 3551 | 3.1 | 91 | 76-89 |
| 4 | 7072 | 2.2 | 39 | 24-37 |
| 8 | 7072 | 2.9 | 78 | 63-76 |

[1]Normalized yield and absolute yield (based on carbonate) are theoretically identical. In practice, there is a discrepancy in the actual normalized yield that is actually reported above and the absolute yield (based on carbonate). The absolute yield in practice, based on carbonate, can be determined by the formula 100 * (moles ODPA formed + moles ODDA formed + moles ODTA formed)/moles of carbonate charged in the reaction mixture. Historically, the absolute yield, based on carbonate, was approximately 2-15% lower than the Normalized Yield.

Thus, high levels of chlorophthalide in feed 4-ClPA can be compensated for with higher amounts of HEGCl catalyst levels. Also contemplated are other phase transfer catalysts that function like HEGCl, including but not limited to catalysts such as tetraalkyl or tetraaryl ammonium or phosphonium halides. An elevated level of these catalysts is expected to also compensate for lower yields caused by elevated chlorophthalide levels in ODPA reactions with 4-ClPA.

Order of Carbonate Addition, and Staged Carbonate Addition.

The following examples demonstrate the importance of order of addition of the carbonate on yield or ODPA. In this embodiment, addition of carbonate to reaction mixtures containing 4-ClPA and catalyst produced a higher yield of ODPA than pre-mixing the 4-ClPA and carbonate before addition of the catalyst.

Materials: Reagent grade o-dichlorobenzene (oDCB) was used as received from Fisher Scientific. Material used in the glove-box had been stored over 4 A molecular sieves and checked for water levels of less than 10 ppm via KF. Solid 4-ClPA having a chlorophthalide level that was more than 250 ppm. and purified via distillation. After distillation, chlorobenzoic acid impurities were below detection limits, and chlorophthalide impurities were present at a level of about 6500 ppm. In some reactions, HEGCl was used as a solid that had been extracted from a brine solution that originally had been purchased from Vandermark. It was stored in the glove box. In most reactions, 35.7% HEGCl in brine solution, purchased commercially, was used. $K_2CO_3$ was obtained from Armand Corporation (Oxychem) and dried at 220° C. in a Kugelrohr overnight, then stored in the glove-box. Extra fine particle size was used, identical to material used on a greater than 100 gal (379 liter) scale.

HEGCl in Brine Solvent Swap & Drying Procedure.

270 mL of oDCB and 5.2 mL of HEGCl solution in brine (35.7% assay; 4 mol %) was weighed out into a 250 ml three-neck flask, which was equipped with a Dean-Stark trap with a condenser, a mechanical stirrer, and a nitrogen inlet. The mixture was heated to 160° C. oil bath temperature and the bulk of water was distilled off as an oDCB/$H_2O$ azeotrope within about 30 min. The temperature was then increased to reflux (210° C. oil bath temperature) and heated for 4.5 hours under nitrogen atmosphere purge in order to dry the reaction mixture by azeotroping out oDCB/water. A total of about 150.0 g of oDCB/water was distilled off. Reaction dryness is determined by sampling the distillate for water to obtain dryness to <20 ppm via Karl-Fischer titration. Sodium chloride (NaCl) crystals were visibly attached to the flask walls. The reaction mixture was cooled down and the apparatus transferred to the glove box.

Examples 9 to 15

One Pot Reactions a) Using HEGCL in Brine Solution:

All glassware was thoroughly dried in an oven at 120° C. prior to use. In the glove-box, about 32.0 g of 4-ClPA and about 12.0 g $K_2CO_3$ (depending on the formulation of excess 4-ClPA) was weighed out into above 250 ml three-neck round-bottom flask, containing the dried HEGCl/NaCl/oDCB solution. The apparatus was equipped with a Dean-Stark trap, a condenser, a mechanical stirrer, and a nitrogen inlet. Material was rinsed from the funnel with small amount of oDCB for formulation accuracy, which had been dried over 4 A molecular sieves (less than 5 ppm of water via KF titration).

b) Using Solid HEGCl:

All glassware was thoroughly dried in an oven at 120° C. prior to use. In the glove-box, about 32.0 g of 4-ClPA, about 12.0 g $K_2CO_3$ & 2 g of HEGCl was weighed out into a 250 ml three-neck round-bottom flask, which was equipped with a Dean-Stark trap, a condenser, a mechanical stirrer, and a nitrogen inlet. oDCB (120 g) was added, which had been dried over 4 A molecular sieves (<5 ppm of water via KF titration).

c) Procedure for Continuous or Staged Carbonate Addition for Both HEGCl Types:

The apparatus was setup in a hood and 4-ClPA completely dissolved in oDCB upon heating. The mixture was heated at reflux (210° C. oil bath temperature) for half an hour under nitrogen atmosphere purge and 50 g of oDCB was distilled off. Vigorous carbon dioxide evolution occurred and the reaction turned yellow in color. Reaction dryness was determined by sampling distillate as below 10 ppm via KF. The reaction was allowed to stir at 210° C. oil bath temperature for 4 or 7 hours. The reaction mixture gradually turned dark yellow to greenish-grey, eventually black & thick. The reaction mixture was cooled overnight, homogenized & analyzed via HPLC.

Examples 16 to 18

Staged $K_2CO_3$ Additions

All glassware was thoroughly dried in an oven at 120° C. prior to use. In the glove-box, about 32.0 g of 4-ClPA was weighed out into above 250 ml three-neck round-bottom flask, containing the dried HEGCl/NaCl/oDCB solution. 4-ClPA was rinsed from the funnel with small amount of oDCB for formulation accuracy, which had been dried over 4 A molecular sieves (<5 ppm of water via KF titration). The apparatus was equipped with a Dean-Stark trap with a condenser, a mechanical stirrer, and a nitrogen inlet outside the glove box in a hood. Several nitrogen adapters equipped with stoppers for adding incremental amounts of $K_2CO_3$ (typically 3.0 g at a time) were set up with $K_2CO_3$ in the glove-box. The charged flask was lowered into a 200° C. oil bath with stirring for 10 minutes to dissolve the material before adding the first 3.0 g $K_2CO_3$ charge. The reaction mixture was stirred for an additional 15 minutes prior to the addition of the remaining carbonate. Details for the carbonate addition are shown in Table 3. A nitrogen sweep was added to distill about 50 g of oDCB/$H_2O$ for drying purposes. Distillate was sampled and checked for dryness by Karl Fisher. The reaction was typically run for 7 hours. The reaction mixture became yellow, orange, and eventually black in color and was very thick at the end of the reaction. The reaction was cooled overnight without stirring. A sample of the reaction mixture (after cooling and homogenization) and an overhead distillate sample were prepped for HPLC.

Examples 19-20

$K_2CO_3$ Powder Addition Funnel Additions

All glassware was thoroughly dried in an oven at 120° C. prior to use. In the glove-box about 32.0 g of 4-ClPA was weighed out into above 250 ml three-neck round-bottom flask, containing the dried HEGCl/NaCl/oDCB solution. The apparatus was equipped with a Dean-Stark trap with a condenser, a mechanical stirrer, and a nitrogen inlet. Material was rinsed from the funnel with small amount of oDCB for formulation accuracy, which had been dried over molecular sieves (less than 5 ppm of water via KF titration). The charged flask was removed from the glove box and set up in the hood with a Dean-Stark trap topped with water-cooled condenser, an oil bubbler, and a mechanical stirrer. The glassware setup was the same as the previous reaction but with only one $N_2$ adapter used to add the first 3.00 g (¼ of the charge) of $K_2CO_3$, and a powder addition funnel to add the remaining 9.00 g of $K_2CO_3$ over 2.75 hours. The charged flask was lowered into 200° C. oil bath with stirring for 10 minutes to dissolve the material before adding the 3.0 g $K_2CO_3$ charge. The reaction was stirred for 15 minutes before switching to a powder addition funnel to add the remaining 9.0 g of $K_2CO_3$. A nitrogen sweep was added to distill about 50 g of oDCB/$H_2O$ for drying purposes. The distillate was sampled and checked by Karl Fisher for dryness. The reaction was typically run for 7 hours. The reaction mixture was allowed to cool overnight with no stirring. The reaction mixture sample was prepared after being cooling and was sampled for analysis by HPLC.

KF titrations were performed as described above. The method of analyzing reaction samples was a reverse phase chromatography method using authentic standards.

Table 3, Examples 9 to 15, summarizes the results of the base case, single pot reaction. In Examples 9-15, the 4-ClPA and carbonate were premixed before addition of the catalyst, producing an average yield of, 81.6% with a standard deviation (STDEV, st. dev) of 1.7%, based on the carbonate. Examples 16 to 20 demonstrate the effect of staged carbonate additions at comparable catalyst level. The results in Table 3 are the average of multiple replicates for each condition. The average yield for Examples 16 to 20 was 87.6% with a st. dev of 2.1 indicating that staged carbonate addition is preferable. In staging Examples 16 to 18, the carbonate was added in 4 equal increments at t=0, 1.5, 2.5 and 3.5 hrs, while in staging Examples 19 to 20, the first quarter of the carbonate was added at t=0 and the remaining carbonate was added continuously starting at t=¼ hr and lasting until t=3 hours. From the results it is clear that the carbonate addition in a staged manner, in particular using the method of Examples 19 to 20, results in improved yield compared to the base case Examples 9 to 15, where all the carbonate was added at the beginning of the reaction. Without being bound by theory, possible causes include minimization of side reactions that lead to a loss of selectivity to the desired product. The yields in table were absolute yields and are defined as moles 100*(ODPA+moles ODTA+moles ODDA in the reaction mixture measured via HPLC)/(moles K2CO3 charged).

TABLE 3

Benefits of staged carbonate addition compared to single pot addition.

| EXAMPLE | Mode of Carbonate addition | 4-ClPA Excess (mol %) | Catalyst level (ppm) | Absolute Yield (%) |
|---|---|---|---|---|
| 9 | Single pot | 3.23 | 4 | 82.68 |
| 10 | Single pot | 2.31 | 4 | 83.46 |
| 11 | Single pot | 2.67 | 4 | 82.37 |
| 12 | Single pot | 2.84 | 4 | 80.44 |
| 13 | Single pot | 2.75 | 4 | 82.75 |
| 14 | Single pot | 3.01 | 4 | 81.07 |
| 15 | Single pot | 2.85 | 4 | 78.43 |
| 16 | Staged with K2CO3 adds at t = 0, 1.5, 2.5, 3.5 | 2.86 | 4 | 87.12 |
| 17 | Staged with K2CO3 adds at t = 0, 1.5, 2.5, 3.5 | 3.44 | 4 | 85.36 |
| 18 | Staged with K2CO3 adds at t = 0, 1.5, 2.5, 3.5 | 3.14 | 4 | 85.95 |
| 19 | Staged with ¼ added at t = 0 and rest added continuously from t = ¼ hr to 3 hrs. | 3.67 | 4 | 90.16 |
| 20 | Staged with ¼ added at t = 0 and rest added continuously from t = ¼ hr to 3 hrs. | 4.74 | 4 | 89.46 |

Examples 21 to 23

Late Carbonate Addition

It was observed that when the process of Examples 1 to 20 was practiced, a certain amount of 4-ClPA remained unreacted. It was postulated that if some or all of the 4-ClPA remaining at the end of reaction was converted to ODPA, the yield of the reaction would increase. The purpose of these examples was to determine whether the remaining 4-ClPA left in the reactor at the end of the reaction (after the yield had reached a plateau) could be substantially converted to product.

Slow carbonate addition reactions were conducted as previously described. The corrections in carbonate and catalyst were made at 5 hours and 7 hours for individual reactions. The corrections were made with 0.7 g of carbonate or 0.7 g of carbonate plus 0.1 g of HEGCl. The reactions were run for an additional 2 hours after the corrections. Reaction samples were taken at the time of correction and were compared against the reaction samples taken at the end of the reaction. The reaction yield was calculated based on the original amount of carbonate added to compare against the baseline reactions.

Table 4 summarizes the three separate experiments that were conducted to assess the effect of late carbonate addition on yield of ODPA. Example 21, the base example, had a yield of 86%, while Example 22 representing late carbonate plus catalyst addition had a yield of 90%. Example 23, representing only late carbonate addition, did not have an increased yield relative to Example 21. These results indicate that both catalyst and carbonate are essential for converting unreacted 4-ClPA remaining at the end of reaction. Without being bound by theory, this also indicates that the catalyst remaining at the end of the reaction is not in an active form capable of participating in the reaction.

TABLE 4

| Reaction | Late Carbonate addition amount (g) | Late catalyst addition amount (g) | Absolute Yield (%) |
|---|---|---|---|
| Example 21 | 0.0 | 0.0 | 86 |
| Example 22 | 0.7 | 0.1 | 90 |
| Example 23 | 0.7 | 0.0 | 86 |

Examples 24 to 26

Effect of Caustic Wash of Reactor

In a manufacturing setting frequently reactors are difficult to clean between reactions, making it necessary to conduct multiple reactions without cleaning or pre-treatment between reactions. Thus, a reaction mixture comprises residue from a prior run. For example, it was observed in Examples 1 to 23 that a certain amount of 4-ClPA remained unreacted after the initial reaction. The purpose of the following examples was to evaluate the effect of cleaning the reactor on the yield of ODPA.

ODPA Reactions (Control, Reactor Cleaning, and No Reactor Cleaning).

All glassware was thoroughly dried in an oven at 120° C. prior to use. Example 24 (control): The HEGCl brine solution, 5.2 mL, (1.86 g HEGCl) and 250 g of oDCB was charged to a clean 250 ml three-neck round-bottom flask, which was equipped with a Dean-Stark trap with a condenser, a mechanical stirrer, and a nitrogen inlet. The mixture was azeotropically dried to remove (120 g solvent) all water, which was confirmed by KF titration. The reaction apparatus was transferred to a dry box with inert conditions to transfer flaked 4-ClPA (32.85 g; 0.180 mol, stored in glove box) and 12.10 g $K_2CO_3$ (0.088 mol; Kugelrohr dried; stored in glove box). 4-ClPA completely dissolved in oDCB upon heating. The mixture was heated at reflux (210° C. oil bath temperature) for 4 hours under nitrogen atmosphere with 50 g of oDCB being distilled off. Reaction dryness was determined by sampling distillate as less than 10 ppm via KF.

Example 25: 6 wt % of the total mass of the above described example 24 reaction mixture was left in the reactor for this reaction, and the identical procedure was used as in Example 24 except the reactor was first cleaned using the following protocol: The cleaning protocol used 30 grams of a 5 wt % caustic solution with agitation at room temperature for 45 minutes. The reactor was then rinsed twice with 30 grams of water. Following this, the HEGCl brine solution was added to the reactor, and the procedure of Example 24 was followed from that point on.

Example 26: 6 wt % of the total mass of the above described Example 25 reaction mixture was left in the reactor for this reaction, and the identical procedure was used as in example 24 except the reactor was not cleaned of this residue in any way. Instead, the HEGCl brine solution was added to the reactor containing this residue from the previous reaction, and the procedure of Example 24 was followed from that point on.

Table 5 shows the effect of reactor cleaning on the reaction yield of ODPA. Example 24 is defined as the control with an 82% yield. Example 25 included 6% residue and a reactor cleaning, yielding 80% ODPA (within the standard deviation of the control reaction+/−2%). Analysis of the second water wash from the reactor cleaning protocol had a pH of 7 demonstrating the effectiveness of the rinse. Also the HPLC analysis of this water wash revealed negligible amount of reaction residuals (100 ppm). Example 25 included 6% residue and no reactor cleaning, yielding 43% ODPA.

TABLE 5

Summary of 4-ODPA Reaction Yields At Various Reactor Conditions

| Reaction | Amount of Residue (mass wt %) | Catalyst Dried | Reactor Cleaned | Absolute Yield |
|---|---|---|---|---|
| Example 24 Base case, Control | 0% | Yes | NA | 82% +/− 2% |
| Example 25 Reactor TREATMENT | 6% | Yes | Yes | 80% +/− 2% |
| Example 26 No reactor TREATMENT | 6% | Yes | No | 43% +/− 2% |

Based on the studies conducted, a small amount of the reaction residuals can significantly lower the yield of ODPA. A reactor cleaning procedure was devised to remove reaction residuals at room temperature, which allowed subsequent reactions to maintain the baseline yield.

While the invention has been described with reference to the embodiments thereof, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A method for preparing an oxydiphthalic anhydride which comprises contacting, under reactive and substantially anhydrous conditions in a reactor, at least one chlorophthalic anhydride containing more than 250 ppm chlorophthalide impurity, based on the chlorophthalic anhydride, with a carbonate of the formula $M_2CO_3$, wherein M is an alkali metal, in the presence of a catalytic proportion of at least one phase transfer catalyst selected from the group consisting of hexaalkylguanidinium halides and alpha,omega-bis(pentaalkylguanidinium)alkane salts, phosphonium salts, pyridinium salts, phosphazenium salts, ammonium salts, and combinations thereof; wherein
the phase transfer catalyst is present in a sufficient amount to prepare the oxydiphthalic anhydride when the chlorophthalide is present in an amount that is more than 1000 ppm; and
the oxydiphthalic anhydride is produced in a yield, based on the carbonate, of at least 70%.

2. The method according to claim 1, wherein the chlorophthalide is present in an amount z>1000 ppm relative to the chlorophthalic anhydride, and the phase transfer catalyst is present in a molar percentage amount, Phase Transfer Catalyst mol %, based on the chlorophthalic anhydride, according to the formula:

Phase Transfer Catalyst mol %=$100Y(0.02+(2\times10^{-6})zK)$;

wherein Y is a number >=1, and
K=(MW of chlorophthalic anhydride)/(MW of the chlorophthalide).

3. The method of claim 2, wherein Y is a number ranging from 1 to 20.

4. The method according to claim 1 wherein the oxydiphthalic anhydride is prepared in batch mode.

5. The method according to claim 1 wherein the oxydiphthalic anhydride is prepared in continuous mode.

6. The method according to claim 1, wherein the oxydiphthalic anhydride is prepared on a scale exceeding 2 kilograms/batch or 2 kilograms/hour.

7. The method according to claim 1, wherein the oxydiphthalic anhydride is prepared on a scale greater than 100 kilogram per batch or 100 kilogram/hour.

8. The method according to claim 1, wherein the catalyst is added to a mixture of the chlorophthalic anhydride and the carbonate at a reaction temperature.

9. The method according to claim 1, wherein the carbonate is added to a mixture of the chlorophthalic anhydride and the phase transfer catalyst at a reaction temperature.

10. The method according to claim 1 wherein the carbonate is present in an amount of about 45 to about 53 mol % relative to chlorophthalic anhydride.

11. The method according to claim 1 wherein the chlorophthalic anhydride is 3-chlorophthalic anhydride, 4-chlorophthalic anhydride, or a mixture thereof.

12. The method according to claim 1 wherein the chlorophthalic anhydride is 4-chlorophthalic anhydride.

13. The method according to claim 1 wherein M is potassium.

14. The method according to claim 1 wherein the carbonate is selected from the group consisting of powdered carbonates, granular carbonates, flaked carbonates, and combinations thereof.

15. The method according to claim 1 wherein a solvent is also present.

16. The method according to claim 15 wherein the solvent is at least one member selected from the group consisting of ortho-dichlorobenzene, para-dichlorobenzene, sulfolane, dimethylacetamide, dichlorotoluene, 2,4-dichlorotoluene, 1,2,4-dichlorobenzene, diphenyl sulfone, phenetole, anisole and veratrole, n-methyl pyrrolidine and mixtures thereof.

17. The method according to claim 15 wherein the solvent is ortho-dichlorobenzene, 2,4-dichlorotoluene or 1,2,4-trichlorobenzene.

18. The method according to claim 1 wherein the phase transfer catalyst is selected from the group consisting of hexaethylguanidinium chloride, hexaethylguanidinium bromide, hexa-n-butylguanidinium bromide, 1,6-bis(N,N',N',N'',N''-penta-n-butylguanidinium)hexane dibromides, 1,6-bis(N-n-butyl-N',N',N'',N''-tetraethylguanidinium)hexane dibromides, and mixtures thereof.

19. The method according to claim 1 wherein the phase transfer catalyst is tetraphenylphosphonium bromide.

20. The method according to claim 1 wherein the yield is greater than 85%.

21. The method according to claim 1 wherein the yield is greater than 90%.

22. A method for preparing 4,4'-oxydiphthalic anhydride which comprises contacting, in a solvent with boiling point greater than about 150° C. under substantially anhydrous conditions in a reactor and at a temperature in the range of about 120° C. to 250° C., 4-chlorophthalic anhydride containing greater than 1000 ppm chlorophthalide impurity with potassium carbonate in the presence of a catalytic proportion of hexaethylguanidinium chloride, the molar ratio of 4-chlorophthalic anhydride to potassium carbonate being in the range of 1.9 to 4 and the proportion of hexaethylguanidinium chloride being in the range of greater than or equal to 2 mol %, and further defined by the formula below, based on 4-chlorophthalic anhydride; wherein the chlorophthalide is present in an amount z>1000 ppm relative to the 4-chlorophthalic anhydride, and the hexaethylguanidinium chloride is present in a molar percentage amount, Phase Transfer Catalyst mol %, based on the 4-chlorophthalic anhydride, according to the following formula:

Phase Transfer Catalyst mol %=$100Y(0.02+(2\times10^{-6})zK)$;

wherein Y is a number >=1, and
K=(MW of 4-chlorophthalic anhydride)/(MW of the chlorophthalide);
wherein the carbonate is present in an amount of about 40 mol % to about 60 mol % relative to 4-chlorophthalic anhydride;
wherein the hexaethylguanidinium chloride is present in a sufficient amount to prepare the 4,4'-oxydiphthalic anhydride when the chlorophthalide is present in an amount that is more than 1000 ppm; and
wherein the 4,4'-oxydiphthalic anhydride is formed in a yield, based on the potassium carbonate, of greater than 70%.

23. The method according to claim 22, wherein the potassium carbonate is added as a powder to a mixture of 4,4'-oxydiphthalic anhydride and hexaethylguanidinium chloride.

24. The method according to claim 22 wherein the solvent is ortho-dichlorobenzene, 2,4-dichlorotoluene, or 1,2,4-trichlorobenzene.

25. A method for preparing an oxydiphthalic anhydride, which comprises:

forming a mixture comprising at least one chlorophthalic anhydride containing greater than 1000 ppm chlorophthalide impurity and a catalytic proportion of at least one phase transfer catalyst selected from the group consisting of hexaalkylguanidinium halides and alpha, omega-bis(pentaalkylguanidinium)alkane salts, phosphonium salts, pyridinium salts; phosphazenium salts, ammonium salts, and combinations thereof; and
incrementally adding to the mixture, dry powder, or slurry under reactive and substantially anhydrous conditions in a reactor, a carbonate of the formula $M_2CO_3$, wherein M is an alkali metal; wherein,
the phase transfer catalyst is present in a sufficient amount to prepare the oxydiphthalic anhydride when the chlorophthalide is present in an amount that is more than 1000 ppm, and the oxydiphthalic anhydride is formed in a yield greater than 70%, based on the carbonate.

26. The method of claim 25, wherein the carbonate is added to the mixture in 2 to 6 stages, or continuously over 0.5 hours to 15 hours, at a temperature of 120° C. to 250° C.

27. The method according to claim 25, wherein the chlorophthalide is present in an amount z greater than or equal to 1000 ppm relative to the chlorophthalic anhydride, and the phase transfer catalyst is present in a molar percentage amount, Phase Transfer Catalyst mol %, based on the chlorophthalic anhydride, according to the following formula:

Phase Transfer Catalyst mol %=$100Y(0.02+(2\times10^{-6})zK)$;

wherein Y is a number >=1, and
K=(MW of chlorophthalic anhydride)/(MW of the chlorophthalide).

28. The method of claim 27, wherein Y is an number ranging from 1 and 20.

29. The method of claim 27, wherein x is a number ranging from 10 to 1000, and z ranges from 1000 to 25000 ppm.

30. The method according to claim 25 wherein the oxydiphthalic anhydride is prepared in batch mode.

31. The method according to claim 25 wherein the oxydiphthalic anhydride is prepared in continuous mode.

32. The method according to claim 25, wherein the oxydiphthalic anhydride is prepared on a scale exceeding 2 kilograms.

33. The method according to claim 25, wherein the oxydiphthalic anhydride is prepared on a scale exceeding 100 kilograms/batch.

34. The method according to claim 25 wherein the carbonate is present in an amount of about 40 mol % to about 60 mol % relative to chlorophthalic anhydride.

35. The method according to claim 25 wherein the chlorophthalic anhydride is 3-chlorophthalic anhydride, 4-chlorophthalic anhydride, or a mixture thereof.

36. The method according to claim 25 wherein the chlorophthalic anhydride is 4-chlorophthalic anhydride.

37. The method according to claim 25 wherein M is potassium.

38. The method according to claim 25 wherein a solvent is also present.

39. The method according to claim 38 wherein the solvent is at least one member selected from the group consisting of ortho-dichlorobenzene, para-dichlorobenzene, sulfolane, dimethylacetamide, dichlorotoluene, 2,4-dichlorotoluene, 1,2,4-dichlorobenzene, diphenyl sulfone, phenetole, anisole and veratrole, and mixtures thereof.

40. The method according to claim 38 wherein the solvent is orthodichlorobenzene, 2,4-dichlorotoluene or 1,2,4-trichlorobenzene.

41. The method according to claim 25 wherein the phase transfer catalyst is selected from the group consisting of hexaethylguanidinium chloride, hexaethylguanidinium bromide, hexa-n-butylguanidinium bromide, 1,6-bis(N,N',N',N'',N''-penta-n-butylguanidinium)hexane dibromides, 1,6-bis(N-n-butyl-N',N',N'',N''-tetraethylguanidinium)hexane dibromides, and combinations thereof.

42. The method according to claim 25 wherein the phase transfer catalyst is tetraphenylphosphonium bromide.

43. The method according to claim 25 wherein the yield is greater than 85%, based on the carbonate.

44. The method according to claim 25 wherein the yield is greater than 90%, based on the carbonate.

45. A method for preparing 4,4'-oxydiphthalic anhydride which comprises:

forming, in a solvent with boiling point greater than about 150° C., a mixture of 4-chlorophthalic anhydride containing greater than 1000 ppm chlorophthalide impurity and a catalytic proportion of hexaethylguanidinium chloride, wherein the proportion of hexaethylguanidinium chloride is in the range of 2 to 10 mole percent based on 4-chlorophthalic anhydride; and
incrementally adding, under substantially anhydrous conditions in a reactor and at a temperature in the range of about 120° C. to 250° C., potassium carbonate, wherein the proportion of potassium carbonate is in the range of 48 mol % to 52 mol % based on 4-chlorophthalic anhydride, wherein
the hexaethylguanidinium chloride is present in a sufficient amount to prepare the 4,4'-oxydiphthalic anhydride when the chlorophthalide is present in an amount that is more than 1,000 ppm, and the 4,4'-oxydiphthalic anhydride is formed in a yield greater than 75%, based on the potassium carbonate.

46. The method according to claim 45, wherein the chlorophthalide is present in an amount z greater than 1000 ppm, and the hexaethylguanidinium chloride is present in a molar percentage amount, Phase transfer catalyst mol %, based on the 4-chlorophthalic anhydride, according to the following formula:

$$\text{Phase Transfer Catalyst mol \%} = 100Y(0.02 + (2 \times 10^{-6})zK);$$

wherein Y is a number $\geq 1$, and
K=(MW of 4-chlorophthalic anhydride)/(MW of the chlorophthalide).

47. The method of claim 1, further comprising pre-treating the reactor by the sequential steps of (i) washing with a caustic solution and removing the caustic solution; (ii) washing with water and removing the wash water; and (iii) repeating steps (ii) one or more times until the wash water has a pH of less than or equal to 7; and wherein the phase transfer catalyst is added in an aqueous solution after the pre-treatment.

48. The method of claim 47, wherein the caustic solution comprises an aqueous solution of sodium hydroxide, wherein the sodium hydroxide is present in an amount ranging from 1 to 20 wt %.

* * * * *